(12) United States Patent
Su et al.

(10) Patent No.: US 11,716,977 B2
(45) Date of Patent: Aug. 8, 2023

(54) CONTINUOUS FEEDING DEVICE FOR PREDATORY MITES AND FEEDING METHOD THEREOF

(71) Applicant: SHIHEZI UNIVERSITY, Shihezi (CN)

(72) Inventors: Jie Su, Shihezi (CN); Jianping Zhang, Shihezi (CN); Zhiping Cai, Shihezi (CN)

(73) Assignee: SHIHEZI UNIVERSITY, Shihezi (CN)

( * ) Notice: Subject to any disclaimer, the term of this patent is extended or adjusted under 35 U.S.C. 154(b) by 0 days.

(21) Appl. No.: 17/955,780

(22) Filed: Sep. 29, 2022

(65) Prior Publication Data

US 2023/0110670 A1     Apr. 13, 2023

(30) Foreign Application Priority Data

Oct. 12, 2021   (CN) .......................... 202111184972.7

(51) Int. Cl.
    *A01K 67/033*     (2006.01)
(52) U.S. Cl.
    CPC ...... *A01K 67/033* (2013.01); *A01K 2227/706* (2013.01)
(58) Field of Classification Search
    CPC .................. A01G 67/033; A01K 2227/706
    See application file for complete search history.

(56) References Cited

U.S. PATENT DOCUMENTS

| 8,327,797 B1 * | 12/2012 | Morales-Ramos .. A01K 67/033 119/6.5 |
| 2010/0119645 A1 * | 5/2010 | Fidgett ................... A01N 63/16 800/9 |
| 2015/0000600 A1 * | 1/2015 | Bolckmans ............ A01N 63/14 119/6.5 |

FOREIGN PATENT DOCUMENTS

| CN | 102318586 A | 1/2012 |
| CN | 104222015 A | 12/2014 |
| CN | 204482760 U | 7/2015 |
| CN | 106070068 A | 11/2016 |
| CN | 206043148 U | 3/2017 |
| CN | 106912455 A | 7/2017 |
| CN | 207720994 U | 8/2018 |
| CN | 208001913 U | 10/2018 |
| CN | 208387668 U | 1/2019 |
| CN | 210168799 U | 3/2020 |
| CN | 210580579 U | 5/2020 |
| CN | 214339509 U | 10/2021 |

* cited by examiner

Primary Examiner — Monica L Perry
Assistant Examiner — Aaron M Rodziwicz
(74) Attorney, Agent, or Firm — Stuart H. Mayer; Mayer & Williams PC (57) ABSTRACT

A continuous feeding device for predatory mites, including a feeding part and an isolation part to solve problems existing in the prior art of accurately controlling a feeding quantity of predatory mites, and reducing a number of the feeding devices required for feeding predatory mites, thereby reducing a feeding cost of predatory mites.

5 Claims, 5 Drawing Sheets

CONTINUOUS FEEDING DEVICE FOR PREDATORY MITES AND FEEDING METHOD THEREOF

CROSS-REFERENCE TO RELATED APPLICATIONS

This application claims priority to Chinese Patent Application No. 202111184972.7, filed on Oct. 12, 2021, the contents of which are hereby incorporated by reference.

TECHNICAL FIELD

The application relates to the technical field of biological control of agricultural pests, and in particular to a continuous feeding device for predatory mites and a feeding method thereof.

BACKGROUND

Predator mites, as important natural enemy arthropods, may feed on a variety of small agricultural pests such as Tetranychus urticae, thrips, Aleyrodidae, etc. Because of a good activity, a large appetite and a strong reproduction of predator mites, they are one of the best biological control agents with commercial prospects at present. There are many kinds of predator mites, and common ones include Neoseiulus cucumeris, Phytoseiulus persimilis, Neoseiulus barkeri and Neoseiulus bicaudus.

Due to characteristics of a rapid reproduction, a low feeding difficulty and a low cost of substitute prey acaroid mites, most of the artificially produced predatory mites have adopted the substitute prey acaroid mites as foods for a propagation and a proliferation. However, due to small sizes and large numbers of mites, conventional inoculation and feeding methods are usually difficult to control a population of the substitute prey acaroid mites and predatory mites, as well as a management in actual production, thus resulting in a waste of materials and products. It is difficult to accurately control a density and a quantity of predatory mite products, so a big difference in product quality is caused, which is not conducive to the commercialization and standardized management.

A continuous feeding may greatly reduce the difficulty of an artificial feeding of predatory mites, improve an operability of a feeding management, and improve a controllability of the product quality of predatory mites. Meanwhile, with an aid of separation means, predatory mites may be separated and harvested gently, which is more conducive to its large-scale production and continuous output of products.

SUMMARY

An objective of the application is to provide a continuous feeding device for predatory mites and a feeding method thereof, so as to solve problems existing in the prior art, realize a continuous feeding of predatory mites, accurately control a feeding quantity of predatory mites, and reduce a number of the feeding devices required for feeding predatory mites, thereby reducing a feeding cost of predatory mites.

To achieve the above objective, the application provides a following scheme: the application provides the continuous feeding device for predatory mites, which includes a feeding part and an isolation part, the feeding part is above the isolation part, and a bottom end of the feeding part is detachably connected with a top end of the isolation part;

the feeding part includes a plurality of feeding assemblies arranged in sequence from top to bottom, and the top and bottom ends of two adjacent feeding assemblies are detachably connected by a connector;

the feeding assemblies include feeding boxes, bottom screens and supporting bases arranged in sequence from top to bottom; the bottom ends of the feeding boxes are fixedly connected with the top ends of the bottom screens, the bottom ends of the bottom screens are fixedly connected with the top ends of the supporting bases, and the bottom end of the supporting base of any feeding box is detachably connected with the top end of an adjacent feeding box through the connector;

climbing pieces for facilitating movements of predatory mites are arranged inside the feeding boxes; and an inducer for inducing predatory mites to move is arranged outside the feeding boxes.

Optionally, the isolation part includes a pool arranged below a lowermost feeding box, and a base is arranged in the pool, the top end of the base is detachably connected with the bottom end of the lowermost feeding box, and a diameter of the lowermost feeding box is smaller than that of the pool.

Optionally, each climbing piece includes a plurality of climbing wires circumferentially arranged in each feeding box, the climbing wires are fixedly connected with inner walls of each feeding box, and the top ends of the climbing wires abut against the bottom end of the bottom screen of the adjacent feeding box.

Optionally, the inducer includes a bracket arranged outside the feeding boxes, and the bracket is provided with an air outlet, and the air outlet is arranged corresponding to the top end of an uppermost feeding box.

Optionally, each connector includes a convex plate fixedly connected with the bottom end of each supporting base, a groove is formed at the top end of any feeding box, the convex plate is matched with the groove, and the two adjacent feeding boxes are detachably connected through the convex plate and the groove.

Optionally, one side of the convex plate close to the groove is fixedly connected with a rubber protective layer, and the rubber protective layer is slidably connected with each feeding box.

Optionally, sterile water is set in the pool, and a ratio of the sterile water is 5%-10% of sodium benzoate, 5%-10% of potassium sorbate and 80%-90% of purified water.

A feeding method of the continuous feeding device for predatory mites includes following steps:

S1, placing prey acaroid mites: putting bran feed containing prey acaroid mites into a first feeding box;

S2, inoculating predatory mites: adding predatory mites into the first feeding box after completing the S1;

S3, stacking the feeding boxes: installing a second feeding box containing prey acaroid mites at the top end of the first feeding box after a number of predatory mites in the first feeding box reaches a predetermined requirement after the S2;

S4, repeatedly stacking the feeding boxes: repeating the S3, and installing a third feeding box containing prey acaroid mites on the top end of the second feeding box containing prey acaroid mites; and S5, harvesting predatory mites: removing the first feeding box after completing the S4, and installing a fourth feeding box containing prey acaroid mites at the top end of the third feeding box, and harvesting all predatory mites in the fourth feeding box after the number of predatory mites in the fourth feeding box reaches the predetermined requirement.

Optionally, in the S3, the second feeding box containing prey acaroid mites is installed when the number of predatory mites is 5-20 mites/g and a density of prey acaroid mites is less than 20 mites/g.

Optionally, in the S5, all predatory mites in the fourth feeding box are harvested when the density of predatory mites in the fourth feeding box is 10-40 mites/g.

The application discloses following technical effects.

Firstly, the isolation part is arranged below the feeding part, so that the isolation part effectively prevents prey acaroid mites and predatory mites from escaping from the feeding part, and avoids a pollution of foreign mite sources and ensure a normal growth and reproduction of predatory mites.

Secondly, the feeding part is a stack of the plurality of feeding boxes. Predatory mites move upward and enter new feeding boxes by using a predatory nature of predatory mites. On the one hand, the feeding of predatory mites is facilitated, on the other hand, a separation of predatory mites from the used feeding boxes is facilitated, thus reducing the number of feeding boxes and facilitating a cleaning of the feeding boxes.

Thirdly, by arranging the climbing pieces and the inducer, the inducer induces predatory mites to move upwards, while the climbing pieces assist predatory mites to move upwards, thus facilitating the separation of predatory mites from the feeding boxes.

BRIEF DESCRIPTION OF THE DRAWINGS

In order to more clearly explain embodiments of the application or technical schemes in the prior art, the following briefly introduces drawings to be used in the embodiments. Obviously, the drawings in the following description are only some embodiments of the application. For those of ordinary skill in the art, other drawings may be obtained according to these drawings without any creative labor.

DETAILED DESCRIPTION OF THE EMBODIMENTS

Technical schemes in embodiments of the application are clearly and completely described below with reference to drawings in the embodiments of the application. Obviously, the described embodiments are only part of the embodiments of the application, but not all of them. Based on the embodiments of the application, all other embodiments obtained by ordinary technicians in the field without creative labor are within a scope of the application.

In order to make the above objects, features and advantages of the application more obvious and understandable, the application is explained in further detail below with reference to the drawings and detailed description.

Figure 1:
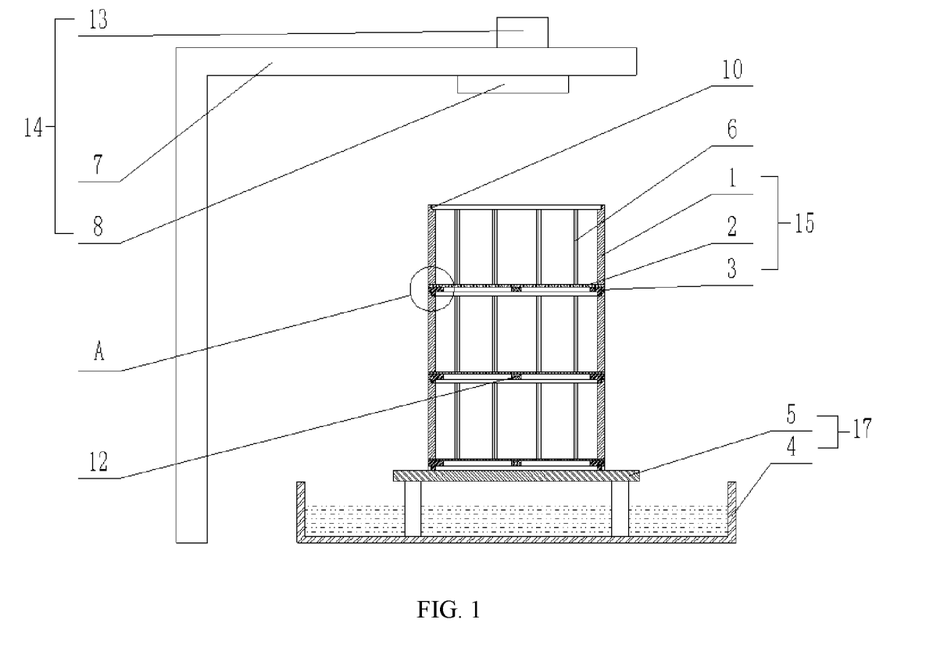
FIG. 1 is a structural diagram of a continuous feeding device for predatory mites.
Figure 2:
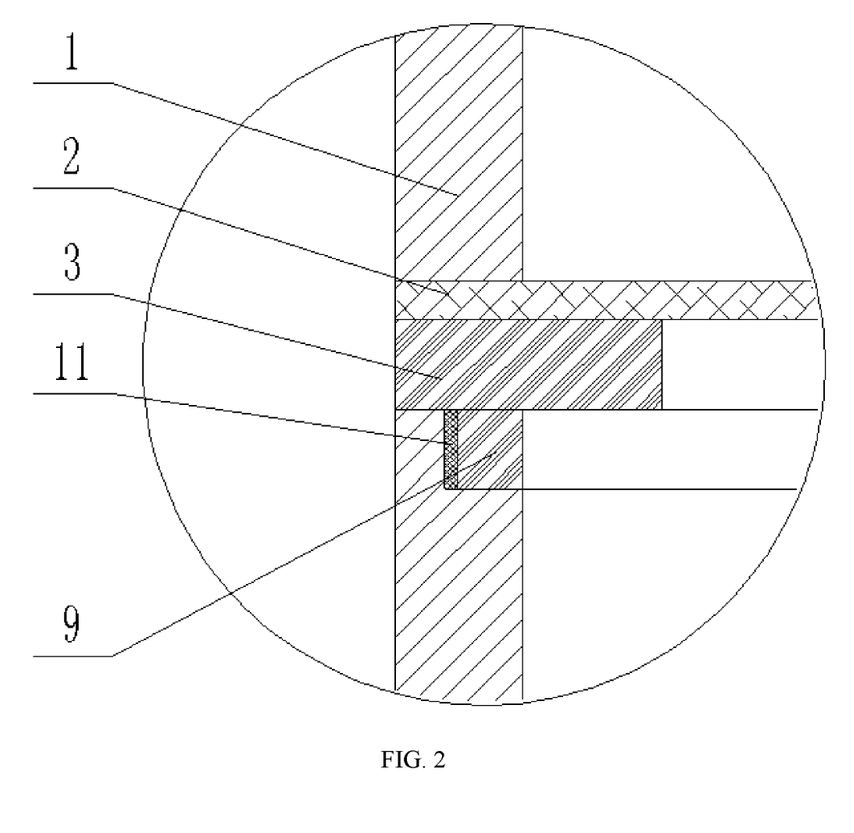
FIG. 2 is a partial enlarged view at A in FIG. 1.
Figure 3:
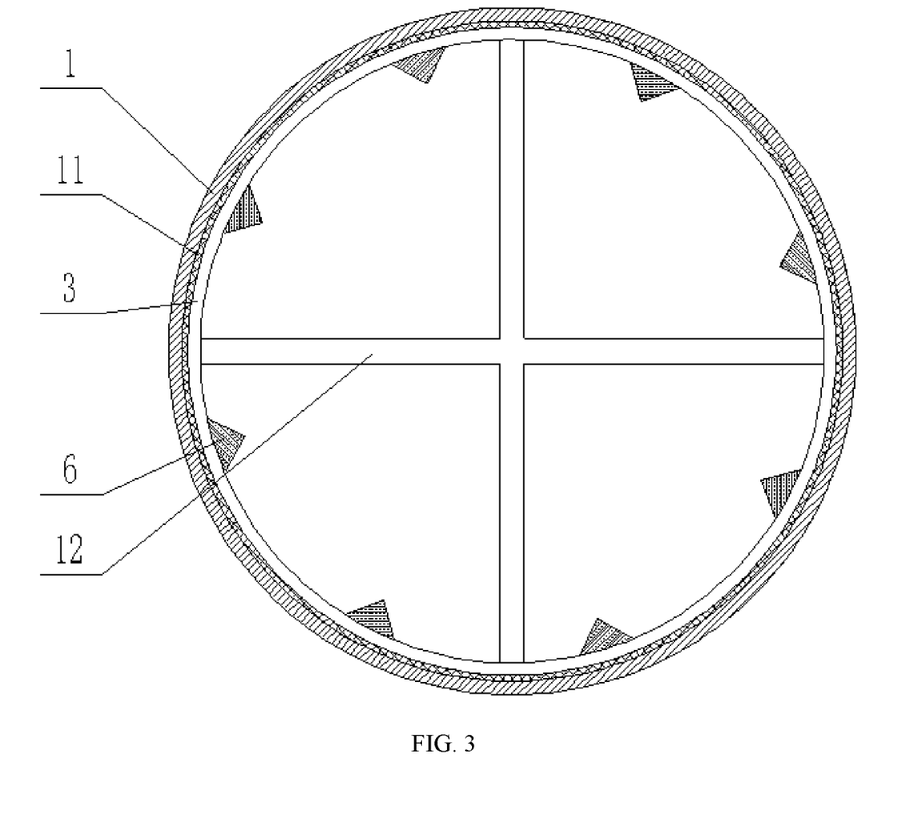
FIG. 3 is a plan view of a continuous feeding device for predatory mites.

The application provides a continuous feeding device for predatory mites, which includes a feeding part and an isolation part 17, the feeding part is above the isolation part 17, and a bottom end of the feeding part is detachably connected with a top end of the isolation part 17; the feeding part includes a plurality of feeding assemblies 15 arranged in sequence from top to bottom, and the top and bottom ends of two adjacent feeding assemblies 15 are detachably connected by a connector; the feeding assemblies 15 include feeding boxes 1, bottom screens 2 and supporting bases 3 which are arranged in sequence from top to bottom; the bottom ends of the feeding boxes 1 are fixedly connected with the top ends of the bottom screens 2, the bottom ends of the bottom screens 2 are fixedly connected with the top ends of the supporting bases 3, and the bottom end of the supporting base 3 of any feeding box 1 is detachably connected with the top end of an adjacent feeding box 1 through the connector; climbing pieces for facilitating movements of predatory mites are arranged inside the feeding boxes 1; and an inducer 14 for inducing predatory mites to move is arranged outside the feeding boxes 1.

Figure 4:
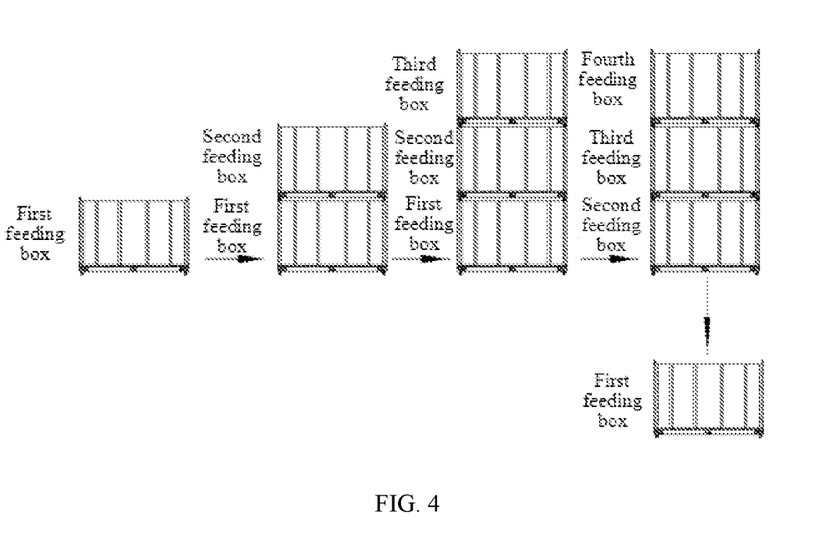
FIG. 4 is a schematic diagram of a breeding process of predatory mites.

Predatory mites are put into the feeding boxes 1 containing prey acaroid mites, and the isolation part 17 is arranged below a lowermost feeding box 1; the isolation part 17 may effectively prevent prey acaroid mites and predatory mites in the feeding part from escaping, and meanwhile may avoid a pollution of external mite sources. When a number of predatory mites in the feeding boxes 1 reaches a predetermined requirement, a second feeding box 1 is installed at the top end of a first feeding box 1, and the inducer 14 starts to work at the same time to induce predatory mites to prey; predatory mites enter the second feeding box 1 under an action of climbing pieces, and after the number of predatory mites in the second feeding box 1 reaches the predetermined requirement, a third feeding box 1 is placed until predatory mites are harvested.

In this technical scheme, each supporting base 3 is of a ring-shaped structure, and a cross-shaped support 12 is fixedly connected in each supporting base 3, and the top end of the cross-shaped support 12 abuts against the bottom end of each bottom screen 2. A function of the cross-shaped support 12 is to support each bottom screen 2 and prevent each bottom screen 2 from being damaged when bran is placed on the bottom screen 2.

In this technical scheme, the feeding boxes 1 are preferably cylinders with hollow top and bottom ends, and materials of the feeding boxes 1 are preferably transparent acrylic plates or polyethylene plates.

In this technical scheme, the top ends of the bottom screens 2 may be fixedly connected with the bottom ends of the feeding boxes 1 by glue, and the bottom screens 2 preferably adopts the screens of 20-100 meshes, so as to facilitate normal movements of predatory mites.

In an embodiment, the isolation part 17 includes a pool 4 arranged below the lowermost feeding box 1, and a base 5 is arranged in the pool 4, the top end of the base 5 is detachably connected with the bottom end of the lowermost feeding box 1, and a diameter of the lowermost feeding box 1 is smaller than that of the pool 4. When feeding predatory mites, the first feeding box 1 is placed on the base 5, and the diameter of the pool 4 is larger than that of the first feeding box 1 in order to prevent predatory mites and prey acaroid mites from escaping.

In this technical scheme, a height of the pool is preferably 3 cm-7 cm, and the height of the base 5 is preferably 5 cm-10 cm, so as to ensure that the bottom end of the lowermost feeding box 1 is not in contact with water in the pool, so that predatory mites normally grow and breed.

In this technical scheme, a connection mode of the base 5 and the lowermost feeding box 1 may be determined according to an actual use situation, as long as the base 5 and the lowermost feeding box 1 are conveniently installed and disassembled; and the connection mode of the base 5 and the lowermost feeding box 1 is preferably the same as that of the two adjacent feeding boxes 1.

In an embodiment, each climbing piece includes a plurality of climbing wires 6 circumferentially arranged in each feeding box 1, the climbing wires 6 are fixedly connected with inner walls of each feeding box 1, and the top ends of the climbing wires 6 abut against the bottom end of the bottom screen 2 of the adjacent feeding box 1. The climbing wires 6 are vertical wires protruding into each feeding box 1, a pitch of each climbing wire 6 is preferably 1 cm, and the height is determined according to the height of each feeding box 1; the bottom ends of the climbing wires 6 are preferably in contact with the bran in one feeding box 1, while the top ends of the climbing wires 6 are preferably in contact with the bottom end of the bottom screen 2 of the other feeding box 1, so as to facilitate the normal movements of predatory mites. The climbing wires 6 are arranged to make use of a natural habit of predatory mites crawling along veins to search for prey when predatory mites are hungry, so as to guide predatory mites to the upper feeding box 1 conveniently.

In an embodiment, the inducer 14 includes a bracket 7 arranged outside the feeding boxes 1, and the bracket 7 is provided with an air outlet 8, and the air outlet 8 is arranged corresponding to the top end of an uppermost feeding box 1. The bracket 7 is arranged outside the feeding boxes 1, and the bracket 7 is used to support the air outlet 8, so that there is an air outlet 8 above each feeding part. An objective of the air outlet 8 is to ensure an air flow inside a plurality of feeding boxes 1, while maintaining an air humidity and an air temperature when feeding predatory mites. The air outlet 8 may effectively transfer a smell of fresh food to the lower feeding box 1 by blowing from top to bottom, and effectively guide predatory mites to crawl upward and transfer to a new feeding box 1.

In this technical scheme, an air outlet area of the air outlet 8 is preferably 20%-80% of the area of each feeding box 1, a distance between the air outlet 8 and the top end of the uppermost feeding box 1 is preferably 5 cm-15 cm, and the air discharged from the air outlet 8 is required to have the humidity of 60%-100%, the temperature of 25° C.-32° C., and an air outlet speed of 2 M-15 M/S. The air outlet 8 is connected with a blower 13 that realizes the above air supply conditions, so as to realize a normal air supply.

In an embodiment, each connector includes a convex plate 9 fixedly connected with the bottom end of each supporting base 3, a groove 10 is formed at the top end of any feeding box 1, the convex plate 9 is matched with the groove 10, and the two adjacent feeding boxes 1 are detachably connected through the convex plate 9 and the groove 10. The bottom end of each feeding box 1 is fixedly connected with one convex plate 9, the convex plate 9 is round, and the groove 10 is opened at the top end of each feeding box 1. Two adjacent feeding boxes 1 are connected together through a cooperation of the convex plate 9 and the groove 10, so the feeding boxes are convenient to disassemble and install and have a high practicability.

In an embodiment, one side of the convex plate 9 close to the groove 10 is fixedly connected with a rubber protective layer 11, and the rubber protective layer 11 is slidably connected with each feeding box 1. On the one hand, the rubber protective layer 11 increases a friction between the two feeding boxes connected together, so as to make the two feeding boxes 1 difficult to separate and improve a firmness of the whole device; on the other hand, the rubber protective layer 11 well blocks a gap between the convex plate 9 and the groove 10, thus preventing a escape of predatory mites and prey acaroid mites.

In an embodiment, sterile water is set in the pool 4, and a ratio of sterile water is 5%-10% of sodium benzoate, 5%-10% of potassium sorbate and 80%-90% of purified water. Sterile water effectively prevents predatory mites and prey acaroid mites from escaping, and effectively blocks an invasion of external mite sources.

Embodiment 1

A feeding method of the continuous feeding device for predatory mites includes operation steps.

Figure 5:
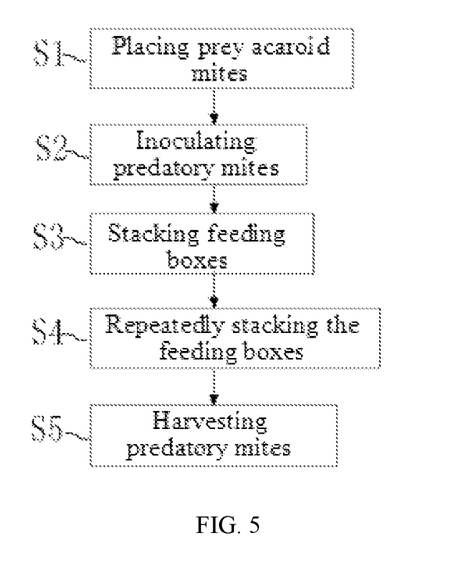
FIG. 5 is a flow chart of a feeding method of predatory mites.

S1, placing prey acaroid mites: putting bran feed containing prey acaroid mites into the first feeding box 1. Before feeding predatory mites, the first feeding box 1 is filled with the bran feed containing prey acaroid mites, in which a population number of acaroid mites is preferably 150-300 mites/g.

S2, inoculating predatory mites: adding predatory mites into the first feeding box 1 after completing the S1. For the first time, the feeding is an inoculation, 50-200 predatory mites are added to the bran feed containing 150-300 prey acaroid mites/g.

S3, stacking the feeding boxes 1: installing the second feeding box 1 containing prey acaroid mites at the top end of the first feeding box 1 after the number of predatory mites in the first feeding box 1 reaches the predetermined requirement after the S2. The number of predatory mites and prey acaroid mites in the first feeding box 1 is monitored. When the number of predatory mites and prey acaroid mites in the first feeding box 1 reaches the predetermined requirement, the second feeding box 1 is installed at the top end of the first feeding box 1, and the air outlet 8 works. As the number of predatory mites in the first feeding box 1 increases, the number of prey acaroid mites decreases, so predatory mites move along the climbing wires 6 to the second feeding box 1.

S4, repeatedly stacking the feeding boxes 1: repeating the S3, and installing the third feeding box 1 containing prey acaroid mites on the top end of the second feeding box 1 containing prey acaroid mites; observing the number of predatory mites and prey acaroid mites in the second feeding box 1, and installing the third feeding box 1 after the number reaches the predetermined requirement.

S5, harvesting predatory mites: removing the first feeding box 1 after completing the S4, and installing a fourth feeding box 1 containing prey acaroid mites at the top end of the third feeding box 1, and harvesting all predatory mites in the fourth feeding box 1 after the number of predatory mites in the fourth feeding box 1 reaches the predetermined requirement. The feeding boxes 1 are preferably kept at 2-4 floors. When the feeding boxes 1 are higher than the 4 floors, the first feeding box 1 is taken out and the fourth feeding box 1 is placed. After a certain time, all predatory mites in the fourth feeding box 1 are harvested.

However, the bran feed in the first feeding box 1 taken out is discarded. After the bran feed is discarded, the first feeding box 1 should be cleaned in time, sterilized at 60° C.-90° C. for 4-12 hours, and then dried before being reused.

In this technical scheme, the continuous feeding of predatory mites requires keeping environmental conditions of the temperature of 25° C.-32° C., a relative humidity of 40%-90% and an air circulation. The number of prey acaroid mites and predatory mites contained in the bran feed in each feeding box 1 is regularly sampled and checked every 3-7 days, and mildews and pollution of the bran are recorded and treated in time.

In an embodiment, in the S3, the second feeding box 1 containing prey acaroid mites is installed when the number of predatory mites is 5-20 mites/g and a density of prey acaroid mites is less than 20 mites/g. Another feeding box 1 may be installed when the number of predatory mites is 5-20 mites/g, or the density of prey acaroid mites is less than 20 mites/g, or a feeding duration is 5-21 days.

In an embodiment, in the S5, all predatory mites in the fourth feeding box 1 are harvested when the density of predatory mites in the fourth feeding box 1 is 10-40 mites/g.

Circulating feeding process: the bran feed containing 200 acaroid mites/g is filled into the first feeding box 1, 100 predatory mites are artificially inoculated, and placed at an ambient temperature of 28° C. and the humidity of 60% for feeding for 10 days. The bran feed containing 200 acaroid mites/g is filled into the second feeding box 1 and stacked on an upper layer of the first feeding box 1 for 7 days. The bran feed containing 200 acaroid mites/g is filled into the third feeding box 1 and stacked on the upper layer of the second feeding box 1 for 5 days. The first feeding box 1 is removed, the bran feed containing 200 acaroid mites/g is filled into the fourth feeding box 1 and stacked on the upper layer of the third feeding box 1 for 5 days. Then, all predatory mites in the fourth feeding box 1 are harvested, and the predatory mite density may reach 20 mites/g.

Embodiment 2

Continuous harvesting and feeding process: the bran feed containing 200 acaroid mites/g is filled into the first feeding box 1, 80 predatory mites are artificially inoculated, and placed at the ambient temperature of 28° C. and the humidity of 60% for feeding for 14 days. The bran feed containing 100 acaroid mites/g is filled into the second feeding box 1 and stacked on the upper layer of the first feeding box 1 for 10 days. The bran feed containing 100 acaroid mites/g is filled into the third feeding box 1 and stacked on the upper layer of the second feeding box 1 for 2 days, and then 1000 predatory mites are separated and harvested from the third feeding box 1 every day for 5 days. The first feeding box 1 is removed, the bran feed containing 200 acaroid mites/g is filled into the fourth feeding box 1 and stacked on the upper layer of the third feeding box 1 for 2 days, and then 1000 predatory mites are separated and harvested from the fourth feeding box 1 every day for 5 days. The second feeding box 1 is removed, the bran feed containing 200 acaroid mites/g is filled into a fifth feeding box 1 and stacked on the upper layer of the fourth feeding box 1 for 2 days, and then 1000 predatory mites are separated and harvested from the fifth feeding box 1 every day for 5 days, so as to continuously harvest predatory mites.

In the description of the application, it should be understood that an orientation or positional relationship indicated by terms "longitudinal", "lateral", "up", "down", "front", "back", "left", "right", "vertical", "horizontal", "top", "bottom", "inner", "outer" and so on are based on the orientation or positional relationship shown in the drawings, only for a convenience of describing the application, rather than indicating or implying that the device or an element referred to must have a specific orientation, be configured and operate in a specific orientation, and therefore cannot be understood as limiting the application.

The above-mentioned embodiments only describe preferred modes of the application, but do not limit the scope of the application. On a premise of not departing from a design spirit of the application, all kinds of modifications and improvements made by ordinary technicians in the field to the technical schemes of the application shall fall within the scope of protection determined by claims of the application.

What is claimed is:

1. A continuous feeding device for predatory mites, comprising:

a feeding part includes a plurality of feeding assemblies and an isolation part includes a pool and a base, wherein the feeding part is on the isolation part, and the feeding assemblies arranged in sequence are detachably connected by a connector with each other and the base of the isolation part;

wherein the feeding assemblies include feeding boxes with top and bottom ends, bottom screens with top and bottom ends and supporting bases with top and bottom ends, which are arranged in a sequence as the feeding boxes are fixedly connected with the top ends of the bottom screens, the bottom ends of the bottom screens are fixedly connected with the top ends of the supporting bases, and the bottom end of the supporting base of any feeding box is detachably connected with the top end of an adjacent feeding box through the connector;

climbing pieces for facilitating movements of predatory mites are arranged inside the feeding boxes;

an inducer for inducing predatory mites to move is arranged outside the feeding boxes;

each climbing piece includes a plurality of climbing wires circumferentially arranged in each feeding box, the climbing wires are fixedly connected with inner walls of each feeding box, and the climbing wires abut against the bottom end of the bottom screen of the adjacent feeding box;

the inducer includes a bracket arranged outside the feeding boxes, wherein the bracket is provided with an air outlet, and the air outlet is arranged corresponding to the top end of an uppermost feeding box; and a second feeding box is installed at a top end of a first feeding box when a number of predatory mites in the feeding boxes reach a predetermined requirement, and the inducer simultaneously induce predatory mites to prey; predatory mites enter the second feeding box under an action of the climbing pieces, and a third feeding box is installed at a top end of the second feeding box until predatory mites are harvested after the number of predatory mites in the second feeding box reach the predetermined requirement.

2. The continuous feeding device for predatory mites according to claim 1, wherein the isolation part comprises a pool arranged below a lowermost feeding box, and a base is arranged in the pool, a top end of the base is detachably connected with a bottom end of the lowermost feeding box, and a diameter of the lowermost feeding box is smaller than that of the pool.

3. The continuous feeding device for predatory mites according to claim 2, wherein sterile water is set in the pool, and a ratio of the sterile water is 5%-10% of sodium benzoate, 5%-10% of potassium sorbate and 80%-90% of purified water.

4. The continuous feeding device for predatory mites according to claim 1, wherein each connector comprises a convex plate fixedly connected with a bottom end of each supporting base, a groove is formed at a top end of any feeding box, the convex plate is matched with the groove, and the two adjacent feeding boxes are detachably connected through the convex plate and the groove.

5. The continuous feeding device for predatory mites according to claim 4, wherein one side of the convex plate close to the groove is fixedly connected with a rubber protective layer, and the rubber protective layer is slidably connected with each feeding box.

* * * * *